United States Patent [19]

Glenn

[11] Patent Number: 4,576,048

[45] Date of Patent: Mar. 18, 1986

[54] METHOD AND APPARATUS FOR ULTRASONIC INSPECTION OF A SOLID WORKPIECE

[75] Inventor: William E. Glenn, Ft. Lauderdale, Fla.

[73] Assignee: New York Institute of Technology, Old Westbury, N.Y.

[21] Appl. No.: 622,227

[22] Filed: Jun. 19, 1984

Related U.S. Application Data

[63] Continuation-in-part of Ser. No. 429,013, Sep. 30, 1982, abandoned.

[51] Int. Cl.⁴ ............................................. G01N 29/00
[52] U.S. Cl. ........................................ 73/642; 73/623; 73/628; 73/629; 310/335
[58] Field of Search ................. 73/642, 626, 625, 628, 73/629, 623; 367/150, 151; 310/334, 335, 336; 181/176

[56] References Cited

U.S. PATENT DOCUMENTS

| | | | |
|---|---|---|---|
| 3,982,142 | 9/1976 | Goble | 367/151 |
| 4,084,582 | 4/1978 | Nigam | 73/620 |
| 4,137,777 | 2/1979 | Haverl et al. | 73/642 |
| 4,241,611 | 12/1980 | Specht et al. | 73/626 |
| 4,252,024 | 2/1981 | Hurwitz | 73/626 |
| 4,321,696 | 3/1982 | Kanda | 310/335 |
| 4,409,839 | 10/1983 | Taenzer | 73/642 |
| 4,481,822 | 11/1984 | Kubota et al. | 73/642 |

FOREIGN PATENT DOCUMENTS 0168156 12/1981 Japan .................................... 73/626

*Primary Examiner*—Stephen A. Kreitman
*Attorney, Agent, or Firm*—Martin Novack

[57] ABSTRACT

The disclosure is directed to a method and apparatus for non-destructive inspection of a solid workpiece, such as a steel workpiece. In accordance with the method of the invention, ultrasound is generated at an annular ring or portion thereof and focused into a hollow substantially cone-shaped beam, or sector thereof. The beam is directed at the surface of the workpiece so as to establish shear mode ultrasound energy in the workpiece. Ultrasound energy is then received from the workpiece (e.g. by reflection or transmission) and characteristics of the internal structure of the workpiece can be determined from the received ultrasound energy. In the preferred embodiment of the invention, the beam is configured such that the ultrasound energy impinging on the surface of the workpiece is at a sufficiently large angle with respect to the normal to the surface such that primarily shear mode of ultrasonic energy will be established within the workpiece. In a form of the invention, a second beam of ultrasound energy is generated and focused within the annular ring, this second beam being used to inspect the workpiece with a compressional mode of ultrasonic energy. In a form of the invention, an ultrasound-reflective surface is disposed in the path of the beam to correct for the inherent focusing effect of the curved surface contour of a workpiece to be inspected.

35 Claims, 9 Drawing Figures

METHOD AND APPARATUS FOR ULTRASONIC INSPECTION OF A SOLID WORKPIECE

This is a continuation-in-part of copending U.S. patent application Ser. No. 429,013, filed Sept. 30, 1982, now abandoned.

BACKGROUND OF THE INVENTION

This invention relates to non-destructive testing and, more particularly, to a method and apparatus for nondestructive inspection of a solid workpiece using ultrasonic energy.

Ultrasonic energy has been used for many years for non-destructive testing of various types of materials. In general, ultrasonic energy is injected into a workpiece to be tested or inspected, and the ultrasonic energy transmitted through or reflected from the workpiece reveals characteristics of the structure of the workpiece. The ultrasonic energy received from the workpiece can be imaged or presented in other ways.

Non-destructive testing frequently uses ultrasound transmission in solids in a shear mode since the velocity of propagation is lower than in the compressional mode and, consequently, the resolution is better. A fluid (such as water) is typically used to couple the ultrasound energy between the transmitting and/or receiving transducer and the solid workpiece to be inspected. Fluids do not support transmission of shear mode waves. Accordingly, a compression mode wave in the fluid is converted to shear mode by inclining the incident beam with respect to the surface of the workpiece.

In steel, for example, conversion of compression mode to primarily shear mode occurs at an angle of approximately 15 degrees with respect to the normal to the workpiece surface. (This results in an angle of beam energy in the steel of about 60 degrees with respect to the normal). This is typically achieved with a small aperture transducer inclined at an angle of about 15 degrees with respect to the normal to the surface. (It can be noted that at angles greater than about 22 degrees, most of the energy is reflected.)

It is among the objects of the present invention to provide a technique which allows inspection in solids such as steel with larger aperture transducers while obtaining the desired shear mode transmission in the workpiece. Among the further objects of the invention are to improve the ultrasonic inspection of solid workpieces with ultrasonic energy in the shear mode, and to provide a technique for inspecting with both shear and compressional mode ultrasonic energy.

SUMMARY OF THE INVENTION

The present invention is directed to a method and apparatus for non-destructive inspection of a solid workpiece, such as a steel workpiece. In accordance with the method of the invention, ultrasound is generated at an annular ring, or portion thereof, and focused into a hollow substantially cone-shaped beam, or sector of a cone. The beam is directed at the surface of the workpiece so as to establish shear mode ultrasound energy in the workpiece. Ultrasound energy is then received from the workpiece (e.g. by reflection or transmission) and characteristics of the internal structure of the workpiece can be determined from the received ultrasound energy.

In the preferred embodiment of the invention, the beam is configured such that the ultrasound energy impinging on the surface of the workpiece is at a sufficiently large angle with respect to the normal to the surface such that primarily shear mode of ultrasonic energy will be established within the workpiece.

In a form of the invention, a second beam of ultrasound energy is generated and focused within the annular ring or portion thereof, this second beam being used to inspect the workpiece with a compressional mode of ultrasonic energy.

In a form of the invention, an ultrasound-reflective surface is disposed in the path of the beam to correct for the inherent focusing effect of the curved surface contour of a workpiece to be inspected, such as from within a cylindrical bore.

In a further form of the invention, a transducer having electrodes in the shape of a curved elliptical arc is advantageously utilized for inspecting from within a cylindrical bore.

Further features and advantages of the invention will become more readily apparent from the following detailed description when taken in conjunction with the accompanying drawings.

DESCRIPTION OF THE PREFERRED EMBODIMENT

Figure 1:
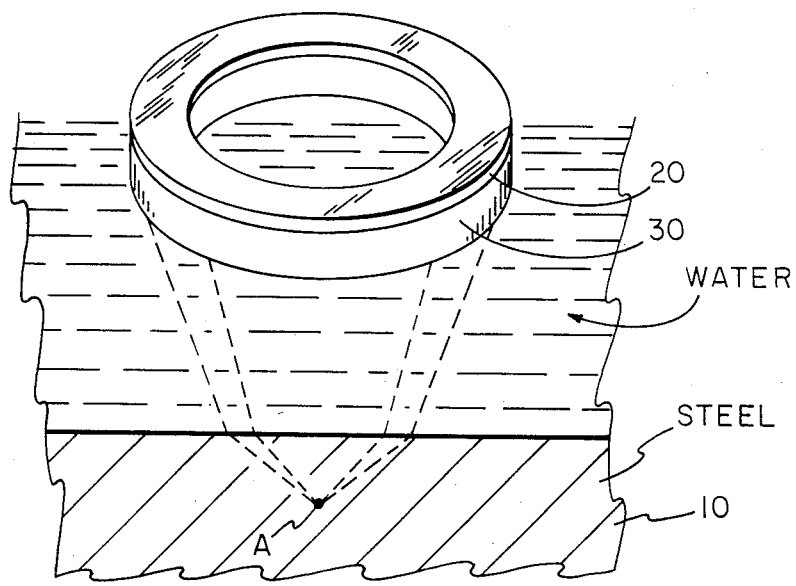
FIG. 1 illustrates a transducer and lens as used in inspection of a workpiece in accordance with an embodiment of the invention.

Referring to FIG. 1, there is shown a simplified diagram which illustrates features of the invention. A transducer 20, in the form of an annular ring of piezoelectric material, is shown as having a focusing lens 30, such as a plastic lens, bonded thereto. The transducer and lens are generally circular, including variations such as elliptical or oval. The lens in this embodiment may or may not have a central aperture. The means for supporting and energizing the transducer are not illustrated in this FIGURE. The transducer and lens are shown as being disposed in a fluid environment, such as water, and the ultrasound beam produced by the transducer and lens is coupled, through the water, to a steel workpiece 10 whose inner structure is to be inspected.

In the present embodiment, the outer cone of the focused ultrasound beam has an aperture of about f/2. Since the beam is formed by the annular ring and focusing means, the cone is hollow. The ultrasound energy impinging on the surface of the steel is at an angle of about 15 degrees with respect to the normal to the surface; i.e., at an angle sufficient to establish primarily shear mode energy in the steel. [In the embodiment hereof, the incident angles range between slightly less than 15 degrees for the innermost rays, to slightly greater than 15 degrees for the outermost rays.] For incident ultrasound energy impinging at an angle of about 15 degrees with respect to the normal to a flat surface, the shear mode energy in the steel will proceed at an angle of about 60 degrees with respect to the normal to the surface. Accordingly, the focused beam is indicated as refracting sharply within the steel to focus at a focal point A.

Figure 2:
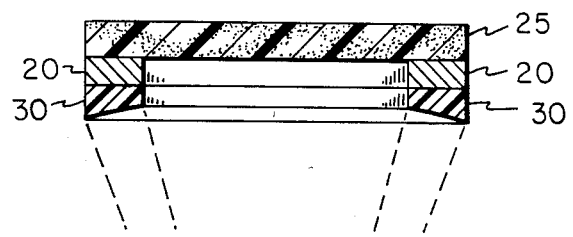
FIG. 2 is a cross-sectional view of the FIG. 1 transducer/lens combination.

FIG. 2 illustrates the transducer 20 and lens 30 in cross-section, with the transducer being mounted on a supportive acoustic absorber 25, such as tungsten-loaded epoxy.

Figure 3:
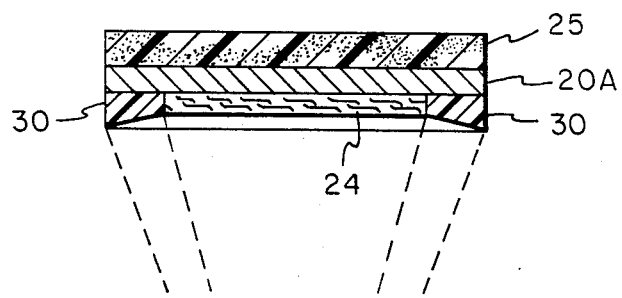
FIG. 3 illustrates a version of the FIG. 1 embodiment which employs a central obfuscation.

FIG. 3 illustrates another arrangement which also yields the desired hollow substantially cone-shaped beam. Backing layer 25 and lens 30 are provided as before, but in this case a disc-shaped (e.g. circular, elliptical, or oval) transducer 20A is provided with an obfuscation 24 centrally positioned to block the central portion of the beam to obtain the desired hollow substantially cone-shaped beam. The obfuscation may be any suitable ultrasound-absorbing material such as rubber or a plastic foam.

Figure 4:
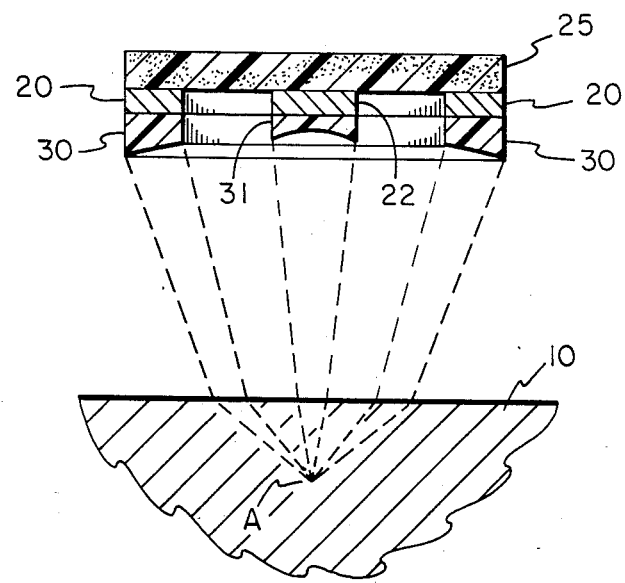
FIGS. 4 and 5 illustrate an embodiment of the invention wherein a second ultrasound beam, used for investigation with compressional mode energy, is employed.
Figure 5:
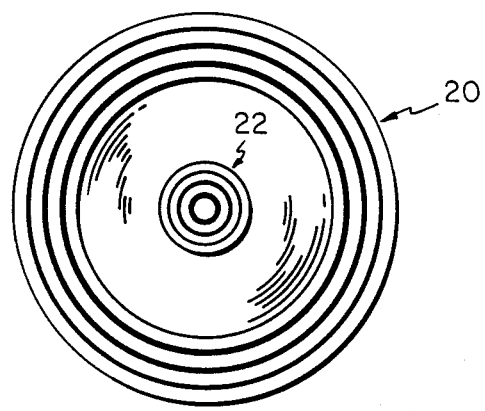

Referring to FIGS. 4 and 5, there is illustrated an embodiment wherein, in addition to an annular transducer 20 and its associated lens 30, used to obtain the hollow substantially cone-shaped beam that provides the shear mode energy in the steel workpiece 10, a central transducer 22 and associated lens 31 are also provided to generate a focused beam which inspects using compressional wave ultrasound energy that results when the beam impinges at less than about 15 degrees with respect to the normal. Both transducers are mounted on acoustic absorber 25. As seen in FIG. 4, the compressional mode focal point can be made to substantially coincide with the shear mode focal point (A). Accordingly, information can be obtained from both ultrasound modes, operated either simultaneously or on a switched basis. Also, dynamic focusing can be employed in conjunction with one or both of the transducers, such as by segmenting the transducers into annular rings (and a central ring, in the case of central transducer 22), the transducer electrode patterns being as shown in FIG. 5.

Figure 6:
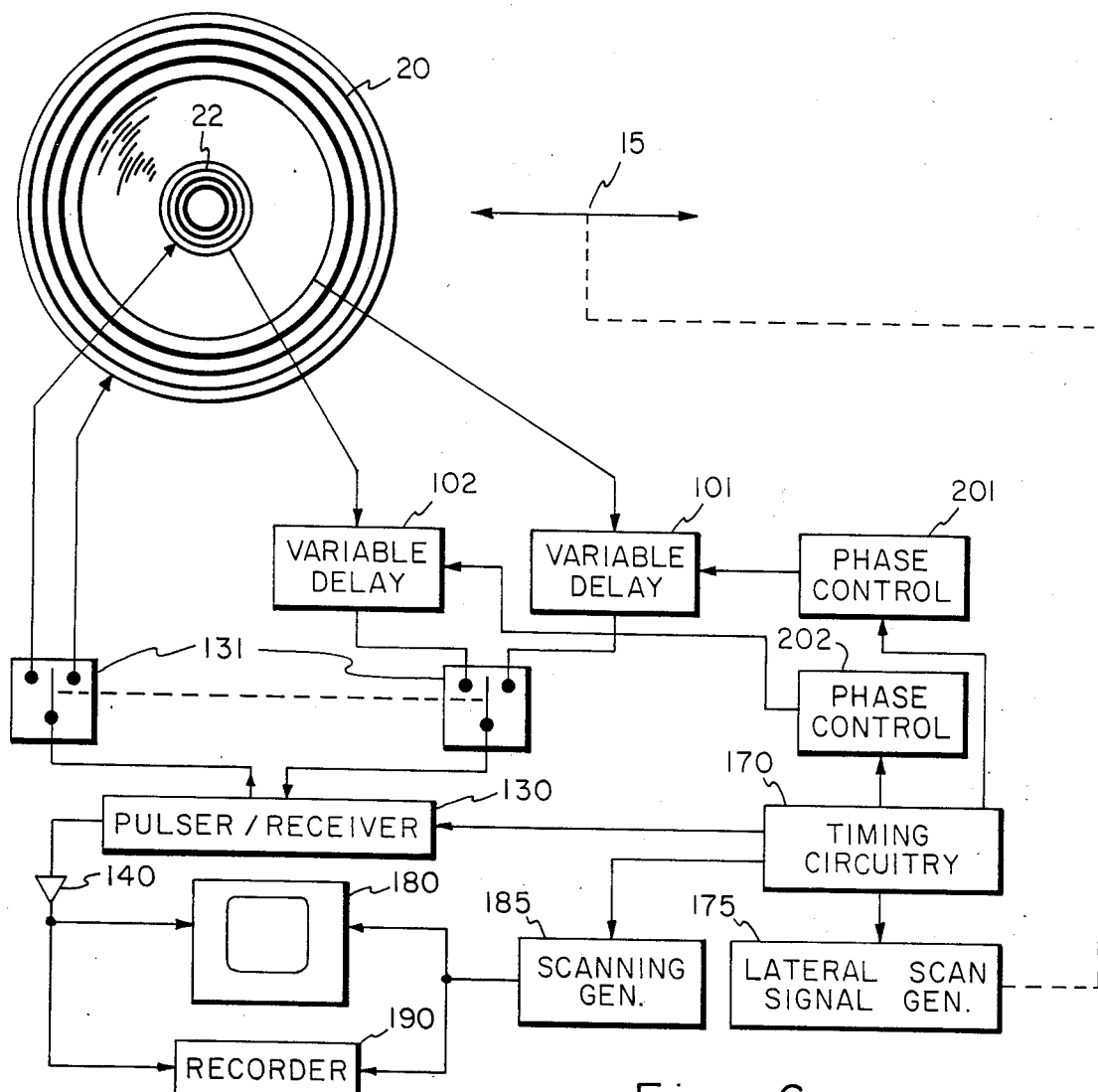
FIG. 6 is a block diagram of an embodiment of the invention as used in an imaging system.

FIG. 6 illustrates the manner in which the focused transducer or transducers hereof can be utilized in an imaging system, it being understood that the ultrasound information from the focused spot in the workpiece can be used to form an image, or in any other desired manner, such as to provide a simple A-scan. In the embodiment of FIG. 6, dynamic focusing is utilized in both the shear mode inspection and the compressional mode inspection, with operator-controllable switching between the two modes. A pulser/receiver 130 is provided, and the pulser output is coupled, through mode selection switch 131, in parallel to either the transducer segments of transducer 20 or transducer 22. Upon reception, the outputs of the transducer segments of the transducers 20 and 22 are respectively coupled to variable delay circuits 101 and 102 where appropriate delays are applied, under control of phase control circuits 201 and 202, to the signals from each transducer segment so as to move the effective focus deeper into the body as a function of time. Dynamic focusing is well known in the art and is not, of itself, an inventive feature hereof. Reference can be made, for example, to U.S. Pat. No. 4,084,582, or to other prior art references which disclose dynamic focusing techniques and systems which relate thereto. The phase control circuitry receives timing signals from timing circuitry 170, which may also be used, as is known in the art, to control a lateral scan of the transducer mechanism, or a mechanical reflector or an electronic scanning mechanism, all as known in the art. Again, the nature of the mechanical or electronic scan is not, of itself, an inventive feature hereof, and reference can be made, for example, to the U.S. Pat. No. 4,084,582, or other prior art which illustrates mechanical or electronic scanning of an ultrasound beam. In the present representation, the output of the timing signal generator 170 is illustrated as being coupled to a lateral scan signal generator 175 which effects lateral scanning of the beam from transducer 20 or 22 as represented by the double-headed arrow 15.

The outputs of variable delay circuitry 101 and 102 are coupled through another section of switch 131 to the receiver portion of pulser/receiver 130, which also conventionally operates under control of timing signals from the timing circuitry 170. The output of the receiver circuitry of pulser/receiver 130 is coupled via amplifier 140 to display 180 and/or video recorder 90, each of which receives scan signals from scan generator 185 that is, in turn, synchronized with the timing circuitry 170.

In operation, the operator can select either the image resulting from the shear mode ultrasound scan or the compressional mode ultrasound scan, in accordance with the mode selection switch 131. If desired, an individual point or points can be viewed in one mode, and then switching can be effected to the other mode to view a given critical portion of the workpiece internal structure or a portion thereof which is believed to have a possible defect. By viewing the workpiece internal structure with both modes of ultrasound energy, an improved knowledge of the workpiece structure can be achieved.

Figure 7:
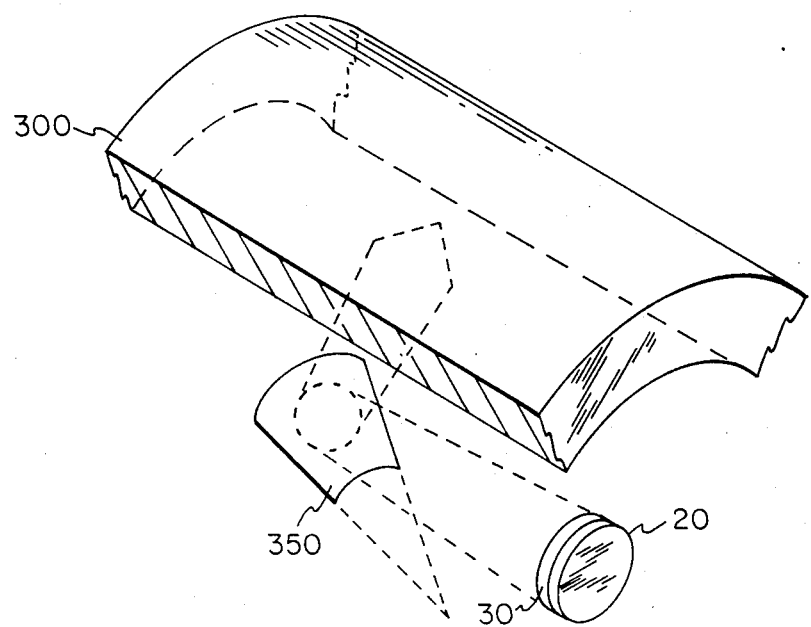
FIG. 7 illustrates an embodiment of the invention wherein a corrective ultrasound-reflective surface is employed.

Referring to FIG. 7, there is shown an embodiment of the invention which employs an ultrasound-reflective surface between the transducer/lens hereof and the curved surface of a workpiece to be inspected. In various applications, where it is desired to inspect the internal structure of a workpiece having a curved surface, a difficulty that can be encountered is the focusing effect of the contour of the curved workpiece surface upon the beam entering and/or leaving the workpiece. In accordance with the presently described feature hereof, a curved ultrasound reflector is provided to correct for the focusing effect of the workpiece surface contour by providing an inverse of the workpiece contour effective focusing. In the illustrative embodiment of FIG. 7, the ultrasound beam from transducer 20 and lens 30 is being used from within the cylindrical bore of a steel workpiece 300 to be inspected. The curvature of the steel surface has a focusing effect on the beam which can be corrected using, in this embodiment, a conical surface 350 forced of an ultrasound-reflective material, such as a metal. In this embodiment, the hollow substantially conical beam from transducer 20 and lens 30 (and, if desired, also the beam from a central transducer, as described above) can be directed approximately parallel to the bore axis, as shown in the FIGURE. The beam is reflected off conical reflective surface 350, impinges on the workpiece surface, and is focused in the workpiece, as shown. The bore can be filled with a fluid such as water or, if desired, a fluidfilled scanning head enclosing the illustrated elements can be provided, in this or the other embodiments. The combination of transducer, lens, and corrective reflective surface can be mounted together, by means not shown, and caused to rotate in the bore and/or move longitudinally in the bore, depending upon the desired inspection pattern. The transducer (or transducers) and lens (or lenses) can be coupled to the type of system illustrated in FIG. 6, and dynamic focusing can be employed, as described.

Figure 8:
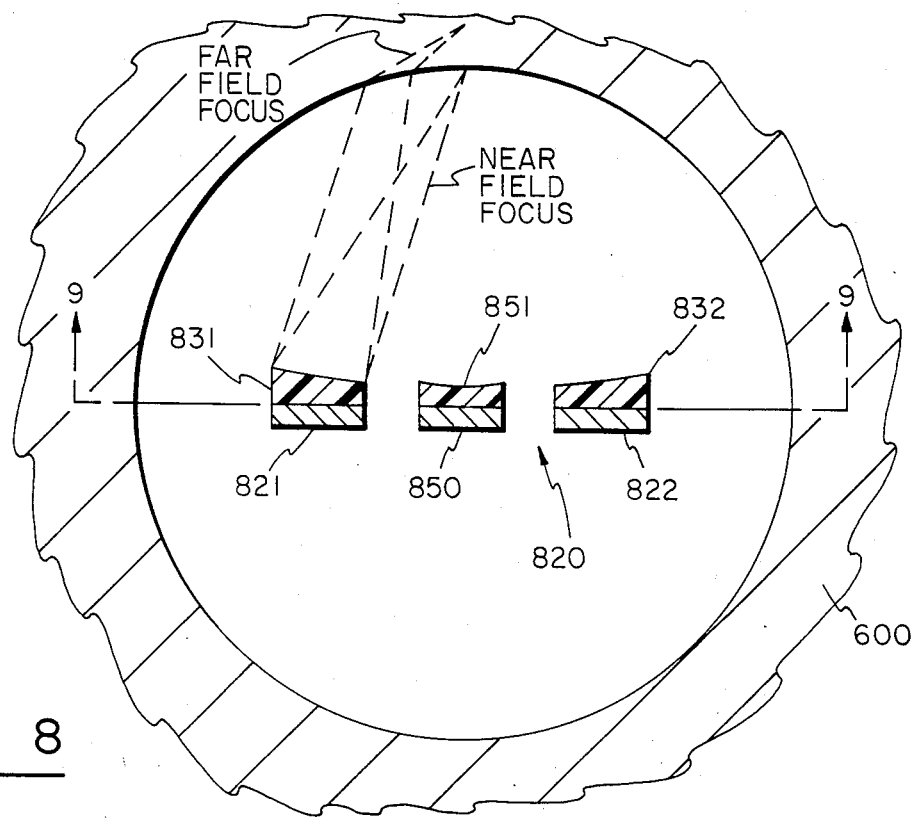
FIG. 8 shows a transducer assembly and lens as used in inspection of a workpiece from within a cylindrical bore.
Figure 9:
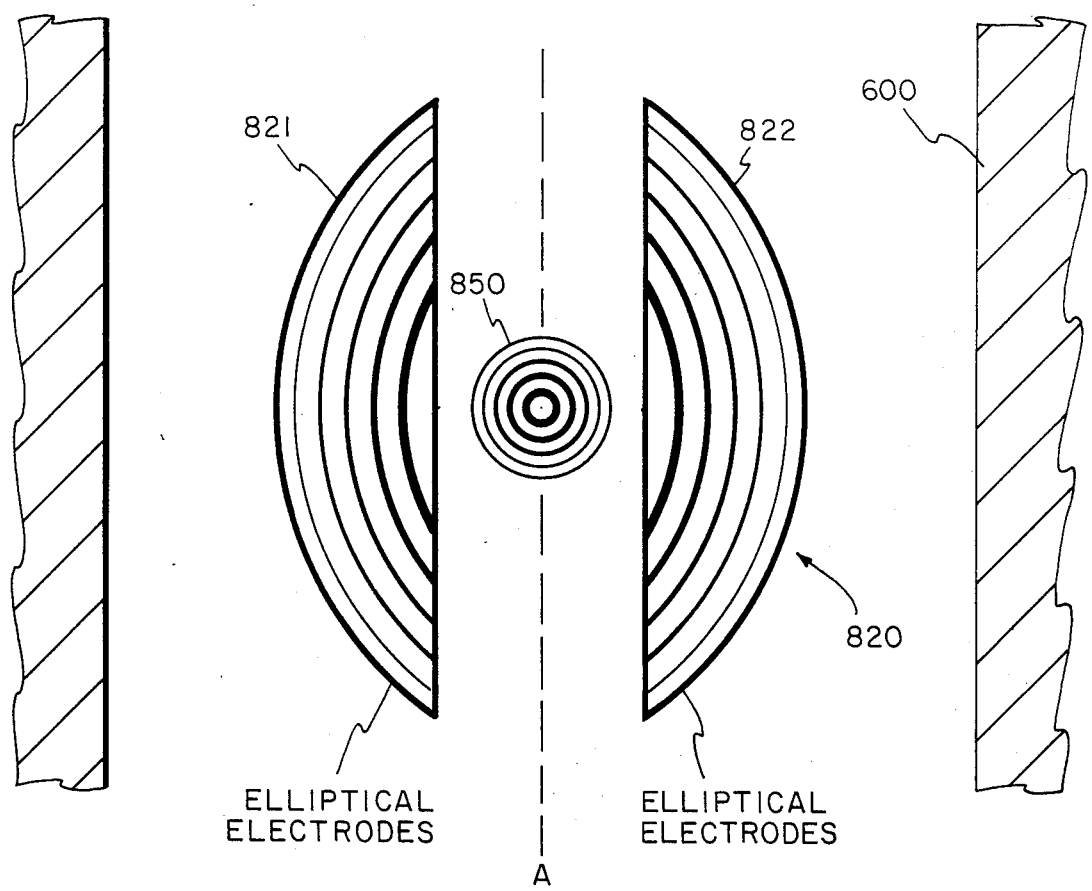
FIG. 9 is a cross-sectional view as taken through a section defined by arrows 9—9 of FIG. 8.

Referring to FIGS. 8 and 9, there is shown an embodiment of a system and technique for inspection from within a steel bore 600, which does not require a separate reflector, and provides improved operation. In this embodiment, a transducer assembly 820 is provided and includes two opposing quadrants 821 and 822 of curved generally annular arc (e.g., elliptical, oval, or circular electrode patterns), which is preferably elliptically shaped. [While quadrants are shown in this embodiment, curved electrode arcs of preferably between about 45 and 135 degrees can be utilized.] The axis of the transducer assembly, in this case, is in the radial direction of the bore, so the transducer assembly faces the wall of the bore. Lenses 831 and 832 are provided, and focus the ultrasound energy into substantially cone-shaped hollow sector beams. The means for supporting and energizing the transducer are not illustrated in the FIGURES.

For substantial depths of penetration into the metal, the quadrants intersecting the axis A of the bore (which are the ones omitted in the present embodiment) cannot meet all of the necessary criteria simultaneously. A transducer that would include these quadrants, in the described orientation, and that will physically fit in the bore, cannot dynamically focus to the desired depth and still achieve the incident angle requirements necessary to convert to shear mode in the metal. Accordingly, only one or both of the two transducer quadrants shown in the FIGS. 8 and 9 are utilized.

For far field inspection, the transducer assembly of FIGS. 8 and 9 can be operated, such as in the type of system illustrated in FIG. 6, by transmitting from one quadrant and receiving from the other. An example of an aproximate far field beam is shown in FIG. 8. For near surface inspection it is advantageous to operate by transmitting and receiving from the same quadrant, so as to remove the problem of specular reflection that is encountered when transmitting and receiving between different quadrants. Single quadrant operation can also be used for far field inspection.

The transducer quadrants shown in FIGS. 8 and 9 are segmented so that adjustable and dynamic focusing can be employed, as described above in conjunction with FIG. 6. The aperture of the beam or beams used is large, as previously described, so the depth of focus tends to be small. Accordingly, the use of electronic adjustable focusing in transmit mode and dynamic focusing in receive mode is important in getting a good signal over a substantial depth of focus. Also, in order to have the beam focal lengths in both the azimuth and axial directions track each other over a reasonable range in depth, the transducer arcs (i.e., the electrodes which define where the energy is generated) are preferably elliptical in shape. This corrects for the influence of the bore curvature on the focus in the azimuth and axial directions.

As seen in FIG. 8 and FIG. 9, a central transducer 850 and associated lens 851 can be provided, as described above, to generate and receive a focused beam which inspects using compressional wave ultrasound energy that impinges on the bore surface at less than about 15 degrees with respect to the normal.

I claim:

1. A method for non-destructive inspection of a solid workpiece, comprising the steps of:
    generating ultrasound energy at a curved arc;
    focusing said ultrasound energy into a substantially cone-shaped hollow sector beam;
    directing said beam at a surface of the workpiece so as to establish shear mode ultrasound energy in the workpiece;
    receiving ultrasound energy from within the workpiece.

2. The method as defined by claim 1 wherein, said curved arc is in the range between about 45 and 135 degrees of arc.

3. The method as defined by claim 1, wherein said curved arc is of elliptical shape.

4. The method as defined by claim 2, wherein said curved arc is of elliptical shape.

5. The method as defined by claim 2, wherein said ultrasound energy is received at said curved arc.

6. The method as defined by claim 1, wherein said ultrasound energy is received from within the workpiece at another curved arc opposing said first-mentioned curved arc.

7. The method as defined by claim 1 further comprising generating further ultrasound energy at a second curved arc opposing said first curved arc; focusing said further ultrasound energy into a further substantially cone-shaped hollow sector beam; directing said further beam at a surface of the workpiece so as to establish shear mode ultrasound energy in the workpiece.

8. The method as defined by claim 1, further comprising the step of determining properties of the workpiece from the received ultrasound energy.

9. The method as defined by claim 1, wherein said workpiece is formed of steel, and wherein the ultrasound energy of said beam impinges on the surface of said workpiece at an angle of about 15 degrees with respect to the normal to said surface.

10. The method as defined by claim 1, further comprising the steps of generating further ultrasound energy in a region within said arc; focusing said further ultrasound energy into a second focused beam; directing said second beam at the surface of the workpiece so as to establish compressional mode energy in the workpiece; and receiving compressional mode energy from within the workpiece.

11. Apparatus for injecting ultrasound energy into a metal workpiece from within a bore in the workpiece, comprising:
    a transducer having electrodes in the shape of a curved elliptical arc;
    means for energizing the transducer; and
    a lens for focusing the ultrasound energy from said transducer into a substantuallly cone-shaped hollow sector beam that is directed toward a surface of the workpiece.

12. Apparatus as defined by claim 11, wherein said curved arc is in the range between about 45 and 135 degrees of arc.

13. Apparatus as defined by claim 11, wherein said transducer and focusing lens are operative to cause the ultrasound energy to impinge on said surface at a sufficiently large angle with respect to the normal to the surface of the workpiece to establish primarily shear mode ultrasound energy in the workpiece.

14. Apparatus as defined by claim 12, wherein said transducer and focusing lens are operative to cause the ultrasound energy to impinge on said surface at a sufficiently large angle with respect to the normal to the surface of the workpiece to establish primarily shear mode ultrasound energy in the workpiece.

15. Apparatus as defined by claim 12, wherein said transducer and focusing lens are operative to cause the ultrasound energy to impinge on said surface at a sufficiently large angle with respect to the normal to the surface of the workpiece to establish primarily shear mode ultrasound energy in the workpiece.

16. Apparatus as defined by claim 11, further comprising means for receiving ultrasound energy reflected from within said workpiece, properties of the workpiece being determinable from the received ultrasound energy.

17. Apparatus as defined by claim 14, further comprising a central transducer; means for energizing said central transducer; and means for focusing the ultrasound energy from said central transducer into a second focused beam which impinges on said workpiece surface to establish compressional mode energy in the workpiece.

18. Apparatus as defined by claim 14, wherein said transducer comprises a plurality of transducer segments adapted for dynamic focusing of said beam.

19. Apparatus as defined by claim 14, wherein the ultrasound energy of said beam impinges on the surface of said workpiece at an angle of about 15 degrees with respect to the normal to said surface.

20. A method for non-destructive inspection of a solid workpiece, comprising the steps of:
generating ultrasound energy at an annular ring;
focusing said ultrasound energy into a substantially cone-shaped hollow beam;
directing said beam at a surface of the workpiece so as to establish shear mode ultrasound energy in the workpiece; and
receiving ultrasound energy from within the workpiece.

21. The method as defined by claim 20, wherein said ultrasound energy impinges on said surface at a sufficiently large angle with respect to the normal to the surface of the workpiece to establish primarily shear mode ultrasound energy in the workpiece.

22. The method as defined by claim 21, wherein said workpiece is formed of steel, and wherein the ultrasound energy of said substantially cone-shaped hollow beam impinges on the surface of said workpiece at an angle of about fifteen degrees with respect to the normal to said surface.

23. The method as defined by claim 20, further comprising the steps of generating ultrasound in a region within said annular ring; focusing said energy into a second focused beam within the region defined by said first beam; directing said second beam at the surface of said workpiece so as to establish compressional mode energy in the workpiece; and receiving compressional mode energy from within the workpiece.

24. The method as defined by claim 20, further comprising the step of determining properties of the workpiece from the received compressional mode ultrasound energy.

25. The method as defined by claim 20, further comprising the step of disposing an ultrasound-reflective surface in the path of said focused ultrasound beam, the reflective surface being shaped to compensate for the focusing effect of the surface contour of the workpiece.

26. The method as defined by claim 25, wherein said workpiece is a cylindrical bore and said ultrasound reflective surface is generally conical.

27. Apparatus for injecting ultrasound energy into a solid workpiece, comprising:
a transducer having an annular active region of piezoelectric material;
means for energizing the transducer;
means for focusing the ultrasound energy from said transducer into a substantially cone-shaped hollow beam that is directed toward a surface of the workpiece.

28. Apparatus as defined by claim 27, wherein said transducer is an annular ring.

29. Apparatus as defined by claim 27, wherein said transducer is generally disc-shaped with a central obfuscation.

30. Apparatus as defined by claim 27, further comprising means for receiving ultrasound energy reflected from within the workpiece.

31. Apparatus as defined by claim 30, wherein said receiving means includes said transducer and focusing means.

32. Apparatus as defined by claim 27, wherein said transducer annular region and focusing means are operative to cause the ultrasound energy to impinge on said surface at a sufficiently large angle with respect to the normal to the surface of the workpiece to establish primarily shear mode ultrasound energy in the workpiece.

33. Apparatus as defined by claim 27, further comprising a central transducer disposed within said annular region; means for energizing said central transducer, and means for focusing the ultrasound energy from said central transducer into a second focused beam within the region defined by said first beam.

34. Apparatus as defined by claim 27, further comprising an ultrasound-reflective surface disposed in the path of said focused ultrasound beam, the reflective surface being shaped to compensate for the focusing effect of the surface contour of the workpiece.

35. Apparatus as defined by claim 34, wherein said workpiece is a cylindrical bore and said ultrasound reflective surface has a generally conical contour.

* * * * *